United States Patent [19]

Flom et al.

[11] Patent Number: 4,641,349
[45] Date of Patent: Feb. 3, 1987

[54] IRIS RECOGNITION SYSTEM

[76] Inventors: Leonard Flom, 1903 Post Rd., Fairfield, Conn. 10403; Aran Safir, 3 Ellsworth Ave., Cambridge, Mass. 02130

[21] Appl. No.: 703,312

[22] Filed: Feb. 20, 1985

[51] Int. Cl.$^4$ ............................................. G06K 9/00
[52] U.S. Cl. ........................................ 382/2; 351/205; 351/206; 354/62; 382/6
[58] Field of Search ............... 382/2, 6; 351/206, 221, 351/208, 205; 354/62; 362/227, 231

[56] References Cited

U.S. PATENT DOCUMENTS

| | | | |
|---|---|---|---|
| 1,192,512 | 7/1916 | Fitz | 351/211 |
| 1,887,115 | 11/1932 | Braun | 351/221 |
| 2,434,890 | 1/1948 | Saunders | 356/214 |
| 3,136,839 | 6/1964 | Safir | 351/211 |
| 3,366,786 | 1/1968 | Delano | 362/231 |
| 3,473,868 | 10/1969 | Young | 351/210 |
| 3,482,904 | 12/1969 | Volk | 351/205 |
| 3,533,683 | 10/1970 | Stark | 351/206 |
| 3,533,684 | 10/1970 | Starh et al. | 351/206 |
| 3,598,107 | 8/1971 | Ishikawa | 351/205 |
| 3,600,098 | 8/1971 | Mohrman | 356/153 |
| 3,778,135 | 12/1973 | Dianetti | 351/221 |
| 3,915,564 | 10/1975 | Urban | 351/206 |
| 3,936,844 | 2/1976 | Matsumura | 354/62 |
| 3,966,310 | 6/1976 | Larson | 351/221 |
| 4,007,980 | 2/1977 | Bracher | 351/219 |
| 4,008,606 | 2/1977 | Talkington | 354/64 |
| 4,023,037 | 5/1977 | Weiss | 250/313 |
| 4,109,237 | 8/1978 | Hill | 382/2 |
| 4,138,714 | 2/1979 | Tsuchihashi | 362/231 |
| 4,172,632 | 10/1979 | Holmes, Jr. | 350/132 |
| 4,189,215 | 2/1980 | Humphrey | 351/39 |
| 4,233,654 | 11/1980 | Tsuchihashi | 362/231 |
| 4,253,743 | 3/1981 | Matsumura | 354/62 |
| 4,257,687 | 3/1981 | Kohayakawa | 354/62 |
| 4,266,861 | 5/1981 | Sawa | 351/206 |
| 4,309,085 | 1/1982 | Morrison | 351/39 |
| 4,375,320 | 3/1983 | Smirmaul | 351/212 |
| 4,393,366 | 7/1983 | Hill | 382/2 |
| 4,523,820 | 6/1985 | Kaakinen | 351/206 |
| 4,533,222 | 8/1985 | Ishikawa | 351/206 |

OTHER PUBLICATIONS

*The Uveal Tract and its Endogenous Inflammations,* Hans Remky, editor, vol. 5, No. 3, Sep. 1965, pp. 630–633.
*Ocular Signs in Slit-Lamp Microscopy,* James H. Doggart, p. 27, (London: 1949).
"Diseases of the Uveal Tract," Duke-Elder and Perkins, in *System of Ophthalmology,* Duke-Edler, Sir Stewart, p. 5 (St. Louis: 1966).
J. Hecht, "Light Modulators Help Crunch Image Data", *High Technology,* (Jan. 1985), pp. 69–72.
C. Simon & I. Goldstein, "A New Scientific Method of Identification", vol. 35, No. 18, *State Journal,* (Sep. 1935), pp. 901–906.

*Primary Examiner*—Leo H. Boudreau
*Assistant Examiner*—Joseph Mancuso
*Attorney, Agent, or Firm*—Ostrolenk, Faber, Gerb & Soffen

[57] ABSTRACT

Methods and apparatus are disclosed for identifying an eye, especially a human eye, on the basis of the visible features of the iris and pupil. The eye is first illuminated until the pupil reaches a predetermined size, at which an image of the iris and pupil is obtained. This image is then compared with stored image information for identification. The stored image information is previously obtained from an eye, the pupil of which was similarly brought to the same predetermined size. The illumination of the iris may include oblique illumination from several positions around the circumference of the iris. The illumination from each position may be relatively monochromatic, so that the resulting shadow will lack the color of the light source at that position, providing better contrast for elevation-depednent features. A system for performing iris recognition may include a processor which controls an illumination control circuit and a camera to obtain images at several predetermined sizes of the pupil.

32 Claims, 12 Drawing Figures

IRIS RECOGNITION SYSTEM

BACKGROUND OF THE INVENTION

1. Field of the Invention

The invention relates to methods and apparatus for identification of physical characteristics of a human being or other animal. More specifically, the invention relates to the recognition of the physical characteristics of the eyes.

2. Description of the Prior Art

Several known techniques are traditionally used to identify a human being from physical characteristics. Fingerprints are one of the best known because of their extensive use by law enforcement agencies. Identification by fingerprint is especially helpful where an individual has left his fingerprint during the commission of a crime, but in general, the technology of fingerprint identification relies heavily on human judgment. In addition, the collection and detection of fingerprints is typically difficult.

More recently, U.S. Pat. No. 4,109,237 has disclosed an identification technique making use of the retinal vasculature patterns of the human eye. Among the advantages of this technique are that it can be automated, and is simpler than detecting, collecting, and identifying fingerprints. Furthermore, although some individuals may attempt to alter their fingerprints in order to avoid identification, altering the retinal vasculature pattern would be difficult and dangerous, and might impair or destroy the vision in that eye.

It would be advantageous to have an identification technique making use of the unique characteristics of the eye but not requiring pupil dilation and the complex alignment procedure of retinal identification, including focusing on the retina and maintaining alignment with the direction of gaze of the subject. It would also be advantageous to have such an identification technique which could be used with minimal cooperation of the subject.

SUMMARY OF THE INVENTION

The present invention is based on the discovery that the iris and pupil of the eye, especially the human eye, may be used for identification. Therefore, the present invention provides an identification technique based upon the recognition of the unique features of the iris and pupil, referred to herein as "iris identification".

Iris identification shares the advantages of retinal identification, but can be performed more easily because the iris and pupil are more readily visible. In addition, some of the features of the iris and pupil are highly regular, providing a geometric pattern which facilitates automatic identification. An important feature of the iris, however, is that its visible features change substantially as the pupil of the eye expands or contracts. Therefore, an important aspect of effective iris identification is to provide a technique which takes into account these changing features.

The method of identification according to the invention includes illuminating an eye, obtaining an image of the iris and pupil of the eye, and comparing the obtained image with stored image information to identify the eye. Illuminating the eye may include driving the pupil of the eye to a predetermined size, which may be done by directing light onto the retina of the eye and adjusting the intensity of the light until the pupil reaches the predetermined size. The pupil may be driven to a plurality of predetermined sizes, and a respective image of the iris and the pupil may be obtained at each of the predetermined sizes. The image obtained at each predetermined pupil size may be compared with stored image information from an eye with the same pupil size.

In another embodiment, illuminating the eye includes obliquely illuminating the iris to provide shadows of elevation-dependent features. The iris may be illuminated by a plurality of spatially separated, relatively monochromatic light sources, so that each shadow of one of the elevation-dependent features will lack a color corresponding to one of the light sources.

The comparing of the obtained image with stored image information may be a point-by-point comparison with a stored reference image. In an alternative form of comparison, a set of descriptors may be derived from the just-obtained image and these descriptors may be compared with reference descriptors derived from a previous image.

The system according to the invention includes means for illuminating an eye, means for obtaining an image of the iris and pupil of the eye, and means for comparing the obtained image with stored image information to make an identification. The illuminating means may include an adjustable light source for illuminating the eye at a selected value. In addition, the illuminating means may include control means which receive the obtained image of the eye and detect the size of the pupil, the control means being operable for adjusting the adjustable light source to a selected light intensity for controlling the size of the pupil. The control means may further be operable to control the size of the pupil to obtain a plurality of predetermined pupil sizes.

The illuminating means may also include a plurality of relatively monochromatic, spatially separated light sources for providing shadows of elevation-dependent features. Each resulting shadow of an elevation-dependent feature will lack a color corresponding to the color of one of the light sources.

The image-obtaining means may include a camera, and the comparing means may include a processor responsive to the output from the camera. The processor may include storage means for storing reference descriptors derived from a previous image, so that the processor may be operable to derive a set of descriptors from the just-obtained image and to compare these descriptors with the reference descriptors stored in the storage means.

Other objects, features and advantages of the invention will be apparent from the following description, together with the accompanying drawings and the appended claims.

DETAILED DESCRIPTION OF THE PREFERRED EMBODIMENTS

I. General Description

Figure 1:
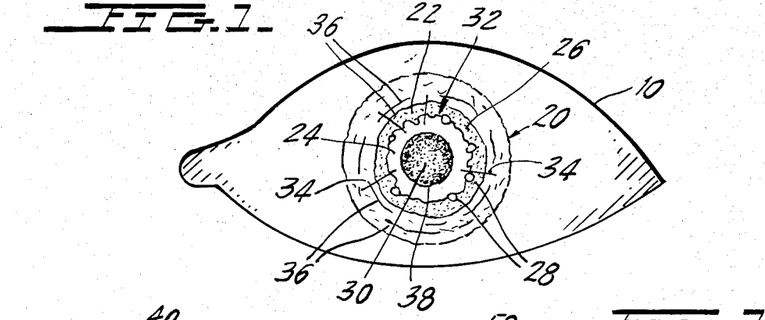
FIG. 1 is a schematic view of the iris and pupil of an eye, showing the major visible features.

FIG. 1 is a simplified drawing of an eye 10, showing in detail the features of the iris 20 and pupil 30. Eye 10, as shown, is a human eye, but some other animals have a similar eye structure, permitting identification by the method of the invention. As shown, pupil 30 is a black, light receptive orifice, while iris 20 may have any of a broad range of hues and may be irregularly pigmented.

The iris 20 and pupil 30 are closely related in function. More precisely, one function of iris 20 is to control the size of pupil 30. Therefore, in addition to the visible features of iris 20 relating to pigmentation, a number of visible features relate to the movements made by iris 20 in order to contract and dilate pupil 30. In general, iris 20 may be divided into the ciliary area 22, which is an annular region at its periphery, and the pupillary area 24, which is an annular area bordering pupil 30. In general, the tissue of iris 20 is soft and loosely woven, and the illumination which enters the pupil 30 and falls on the retina of eye 10 controls muscles in iris 20 causing the size of pupil 30 to grow larger or smaller to regulate the amount of light entering pupil 30. The change in the size of pupil 30 results from involuntary reflexes and is not under conscious control.

Among the pigment-related features of iris 20 are pigment spots 26, some types of which are known as moles, freckles, or nevi, and crypts 28. Pigment spots 26 are random concentrations of pigment-bearing cells in the visible surface of the iris 20, and generally appear in the ciliary area 22. The color of the pigment spots 26 may be nearly black—darker than the darkest brown iris 20. In general, pigment spots 26 are quite stable in number, position and color. Crypts 28, unlike pigment spots 26, relate both to pigmentation and to the surface structure of the iris 20. Iris 20 includes an anterior layer which is directly visible and a posterior layer behind it, which is very darkly pigmented. The anterior layer ranges in pigment from a very light, almost white color to a dark brown color. If the anterior layer is very light or white, the iris 20 appears blue due to the pigment in the posterior layer, and if iris 20 is relatively light in color, the areas in which it is relatively thin will appear somewhat darker, due to the dark color of the posterior layer. These darkened areas may occur, for example, in the features referred to as crypts 28, which resemble sharply demarcated excavations and are typically located adjacent to the collarette 32, the boundary between ciliary area 22 and pupillary area 24.

In addition to the pigment-related features of the iris 20, several other visible features relate to its function of controlling the size of pupil 30. Collarette 32, discussed briefly above, is the boundary between the ciliary area 22 and the pupillary area 24, and is typicallly a sinuous line which forms an elevated ridge running roughly parallel with the margin of the pupil 30. The collarette 32 is the thickest part of iris 20.

Extending radially in relation to the center of pupil 30 are radial furrows 34. A typical radial furrow 34 may begin near pupil 30 and extend through collarette 32. Radial furrows 34 are creases in the anterior layer of iris 20, from which loose tissue may bulge outward, and it is this loose tissue which permits the iris 20 to expand or contract, changing the size of pupil 30. The positions of radial furrows 34 in relation to each other are stable.

Similarly, concentric furrows 36 are creases from which loose tissue may bulge outward, but their shape is generally circular, concentric with the pupil, so that they permit expansion and contraction of the iris in a different direction than radial furrows 34. Concentric furrows 36 typically appear in the ciliary area 22, near the periphery of iris 20.

Eye 10 may also have any of several rare anomalous visible features (not shown) unrelated to pigment or to controlling the size of pupil 30. Due to aging or trauma, atrophic areas may appear on iris 20, resulting in a "moth-eaten" texture. Tumors may grow on the iris. Congenital filaments may occur connecting the iris to the lens of the eye.

Finally, the most striking visible feature of eye 10 is typically pupil 30. As shown in FIG. 1, pupil 30 may not be exactly circular in shape, and its deviation from a circle is a visible characteristic. At the margin of pupil 30 is a protruding portion of the posterior layer of iris 20, the pigment frill 38. Pigment frill 38 typically has a very dark brown color.

The present invention, as discussed above, is based on the discovery that the iris of the eye may be used for identification. This discovery involves both the uniqueness of the iris and the stability of the iris over time. It has been discovered that every iris is unique, particularly in the detailed structure of the front or anterior layer. Not only are the irises of the eyes of identical twins different, but the iris of each eye of any person is different from that of his other eye. Furthermore, although specific details of the appearance of an iris vary dramatically, depending on level and direction of illumination, the basic, significant features of the iris remain extremely stable and do not change over a period of many years. Even features which do develop over time, such as the atrophic areas discussed above, usually develop rather slowly, so that an updated iris image will permit identification for a substantial length of time. A sudden or rapid change in such a feature may result in a failure to identify an individual, but this may alert the individual to the possibility of pathology of the eye. In general, the visible features of the iris and pupil may be used to identify an eye.

Figure 2:
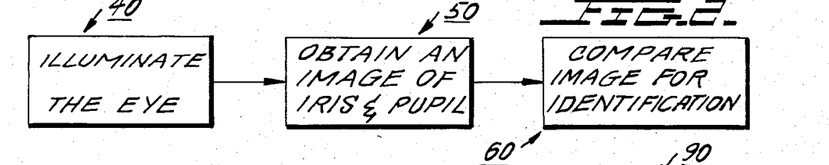
FIG. 2 is a general flow chart showing the major functions performed in the method of the invention.

The method of the invention may be generally understood from FIG. 2, a flow chart showing the basic functions performed in identifying an eye from the visible features of the iris and pupil. As shown in block 40, the first function is to illuminate the eye. Because the visible features of iris 20 and pupil 30 vary depending on illumination, the illumination of the eye will be performed to obtain a desired set of features. Then, in block 50, an image of iris 20 and pupil 30 is obtained, including the desired features. In block 60, this image is compared with stored image information in order to identify the eye.

Figures 3, 4:
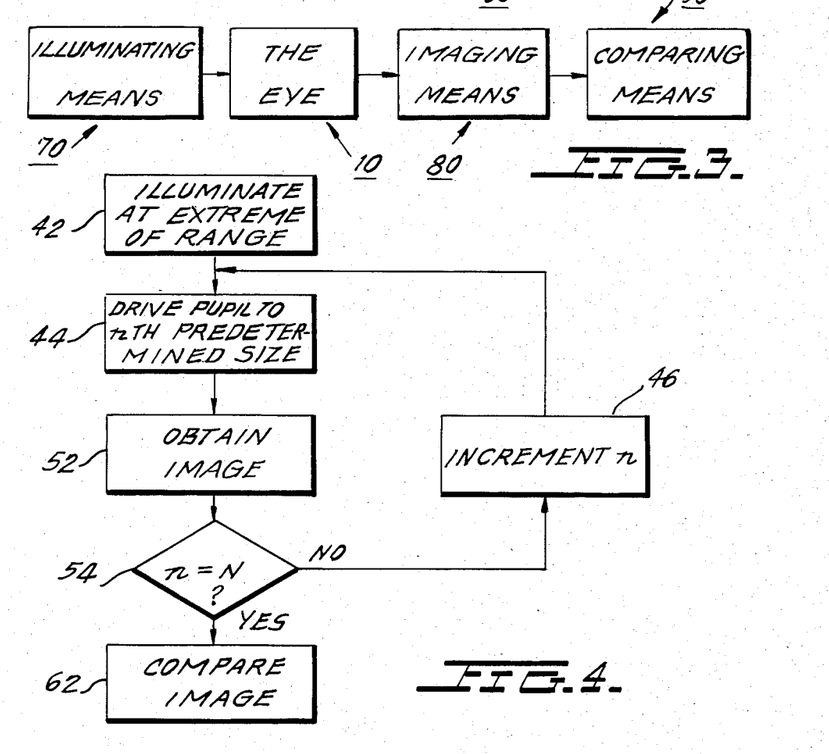
FIG. 3 is a simplified block diagram showing the flow of information through a system according to the invention.
FIG. 4 is a flow chart showing in greater detail an embodiment of the method of FIG. 2.

FIG. 3 is a block diagram showing the major functional components of the system according to the invention. Illuminating means 70 provides light having desired characteristics to the eye 10 under observation. Eye 10 responds to the illumination provided, so that iris 20 and pupil 30 take a characteristic shape. In addition, iris 20 reflects light to imaging means 80, which obtains an image of iris 20 and pupil 30. This image is then compared with stored image information by comparing means 90 in order to identify the eye.

From these basic principles, a variety of methods and systems may be provided for identifying an eye from the iris and pupil.

II. Methods of Identification

A number of methods for implementing the invention are shown in FIGS. 4-7. Each of these figures is a flow chart showing a sequence of steps performed in a process of identifying an eye from the iris and pupil.

FIG. 4 shows a basic method of performing the invention in which the pupil is driven to at least one predetermined size at which an image is taken. In step 42, the pupil is illuminated at one extreme of the range of illumination, either an extreme of darkness or of brightness. The extreme may be determined by the capabilities of the system or may be arrived at by a straightforward series of steps. For example, the illumination may gradually be increased from a moderate level of illumination to an illumination beyond which further illumination does not decrease the size of the pupil. A more efficient approach, however, is to drive the pupil until its size is larger or smaller than the largest or smallest of the predetermined sizes at which an image will be obtained. From this extreme illumination, it will then be possible to drive the pupil to the predetermined size for imaging.

From the size which it has after step 42, the pupil is driven to the first predetermined size in step 44. Assuming that the extreme of illumination was darkness, the illumination will be increased in step 44 until the pupil contracts to a predetermined size. When the pupil reaches this size, an image is obtained and stored in step 52 for subsequent comparison. Then, in step 54, a test is run to determine whether the number n, a count of the images obtained, is greater than or equal to the number N of predetermined sizes at which images are to be obtained. If not, the count of the images obtained, n, is incremented in step 46, and steps 44, 52 and 54 are repeated for the next predetermined size. When all of the predetermined sizes have been imaged, step 54 will determine that n is equal to N, and image comparison will be done in step 62. In step 62, the image at each of the N predetermined sizes is compared with stored image information obtained from an eye illuminated to have the same predetermined pupil size.

Many variations may be made in the basic method of FIG. 4. For example, the largest size which the pupil attains as illumination is decreased could be treated as the first predetermined size, so that an image would be obtained after step 42. If the maximum size of the pupil remains relatively constant over time, this size will be valuable as a descriptor of the eye.

Figure 5:
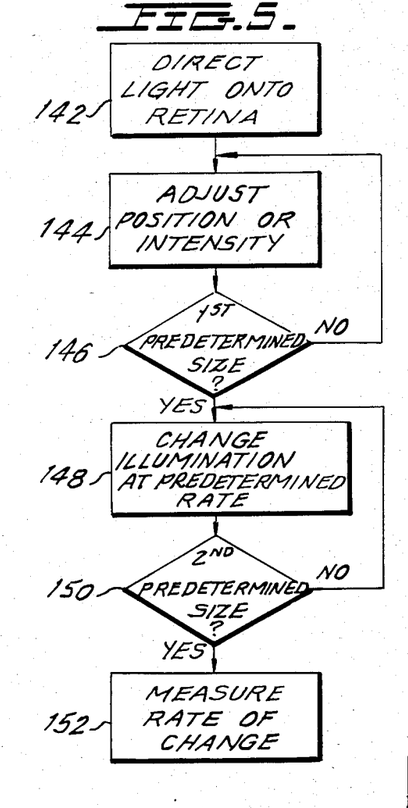
FIG. 5 is a flow chart showing a method of measuring rate of pupil size change according to the invention.

FIG. 5 illustrates another variation which can be made in the basic method of the invention. This variation includes measuring the rate at which the pupil size changes between two predetermined sizes. In step 142, light from a light source is directed onto the retina of the eye in order to control the size of the pupil through reflex action. Then, in step 144, the position or intensity of the light source is adjusted in order to obtain the first predetermined pupil size. In other words, as an alternative to varying the light intensity, the light source may be moved from a central position in which it directs light onto the central area of the retina toward an oblique position in which it directs light at an angle through the pupil onto the more peripheral parts of the retina, or vice versa. After each adjustment, in step 144, a test is performed in step 146 to determine whether the first predetermined size has been obtained. If not, the adjustment is again performed in step 144, and this loop is repeated until the first predetermined size is obtained.

After the first predetermined size is obtained, the illumination of the retina is changed at a predetermined rate in step 148. The changing of the illumination is continued until the test in step 150 determines that a second predetermined size has been attained. At that point, the time necessary to go from the first predetermined size to the second predetermined size at the predetermined rate will provide a measure of the rate of change, in step 152. This measure could also be related to the change in size between the first and second predetermined size and to the specific predetermined rate at which the illumination is changed in step 148. The resulting value may then be used to identify the eye. It should be borne in mind, however, that the rate of change of pupil size may vary for individuals whose reflexes are affected by emotion, drugs, and so forth, so that the rate of change of pupil diameter should generally provide only a secondary indication of identity.

The methods shown in FIGS. 4 and 5 could be combined in a simple manner by making minor modifications to the steps performed in FIG. 4. Step 44 could first be performed to obtain the first predetermined size, corresponding to steps 144 and 146 in FIG. 5. After the performance of steps 52, 54 and 46, step 44 could again be performed by changing the illumination at the predetermined rate to obtain the second predetermined size, corresponding to steps 148 and 150 in FIG. 5. Then, in addition to obtaining the image in step 52, the rate of change of pupil size could also be determined in step 152.

Figure 6:
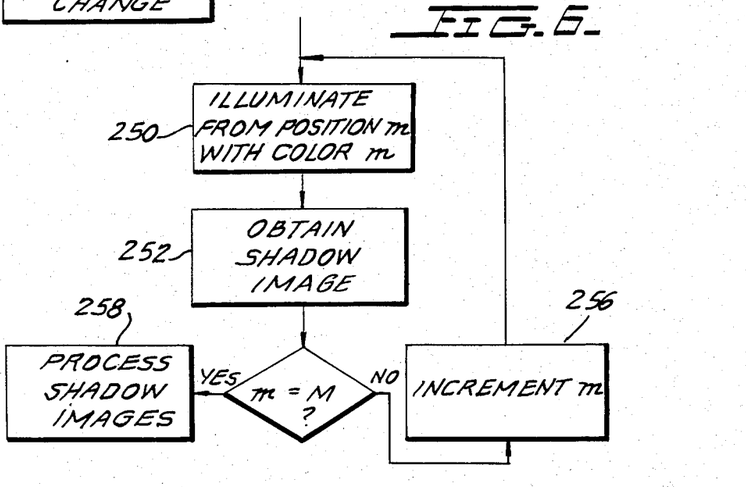
FIG. 6 is a simplified flow chart showing a method of side illumination according to the invention.

FIG. 6 illustrates a routine which may similarly be included in step 52 of FIG. 4, to obtain an image of the iris of an eye in which the elevation-dependent features are shown with greater contrast. This is done by illuminating the iris from a plurality of oblique positions. The illumination from each position is provided by a relatively monochromatic light source to produce shadows of elevation-dependent features lacking the color of that light source. In step 250, illumination from position m is performed using the color m of the corresponding relatively monochromatic light source. This illumination will produce shadows lacking the color m, and an image of these shadows is obtained in step 252. Then, in step 254, a test is performed to determine whether m has reached M, the total number of positions from which the iris is to be illuminated. If not, m is incremented in step 256, and the loop including steps 250, 252 and 254 is repeated until m equals M. When m reaches M, the shadow images may be processed in step 258 to prepare them for subsequent comparison with reference images.

The method of FIG. 6 is especially beneficial for obtaining images of elevation-dependent features such as radial furrows 34. As can be seen from FIG. 1, however, radial furrows 34 may extend radially in any direction, so that illumination from any one direction will provide an excellent shadow image of radial furrows 34 which extend perpendicular to that direction of illumination. Radial furrows which extend parallel to the direction of illumination, however, will produce poor shadow images. Therefore, to produce the best images of radial furrows 34, it is desirable to obtain a number of shadow images and to combine them in processing step 258.

The comparison of images having the same pupil sizes in step 62 of FIG. 4 may be performed in many ways. Onr straightforward method would be to store the reference image as a pixel-by-pixel image resulting from a scanning camera such as a conventional video camera. The image obtained would then be obtained with a similar video camersa, as discussed below in relation to FIG. 8, to obtain a pixel-by-pixel image of the eye. The two images could then be compared, pixel-by-pixel, to determine whether they were the same image. The comparison could be made in a way which would take into account differences in the overall intensity of the two images. This method of comparison, although simple to implement, is extremely sensitive to registration. In other words, the test would only result in a conclusion that the two images were of the same eye if the eyes shown in the two images were of the same size and were positioned identically. Therefore, it will be preferable to perform a comparison algorithm which is not so sensitive to registration.

One comparison algorithm which would not be so sensitive to registration is the correlation algorithm, which has many variations. The effect of an offset in the positioning of the two images could be eliminated based on an algorithm for determining the center of gravity of the pupil in each image. These algorithms could thus be combined to reduce registration sensitivity.

Another comparison method which would not be highly sensitive to registration would be a method using optical signal processing. Hecht, J., "Light Modulators Help Crunch Image Data", *High Technology*, Vol. 5, No. 1 (January, 1985), p. 69-70, 72, discusses techniques for optical comparison which would be readily applicable to the present invention.

Figure 7:
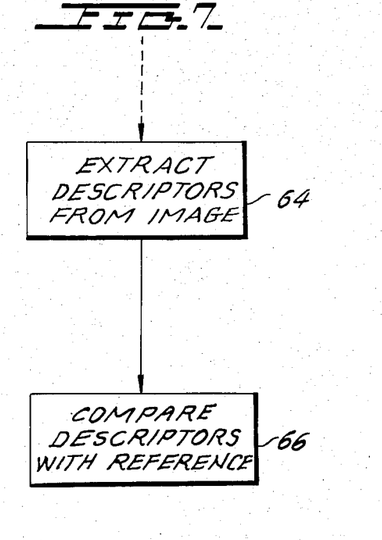
FIG. 7 is a general flow chart showing a method of comparing according to the invention.

FIG. 7 illustrates another method of comparison which could be used in the present invention. In step 64, descriptors are extracted from the image obtained, which may be the image obtained in step 52 of FIG. 4. One example of descriptors which could be extracted would be the angular positions and lengths of the radial furrows 34. Another set of descriptors would be the shape of the pupil 30 or of the pigment frill 38. Other descriptor sets could be obtained relating to the positions and sizes of pigment spots 26, crypts 28 and anomalous features such as atrophic areas, tumors and congenital filaments. Similarly, generally circular features such as collarettes 32 and concentric furrows 36 could be described respective descriptors. All of these descriptors would then be compared with the descriptors of a reference image in step 66. Because several features of the iris 20 and pupil 30 lend themselves readily to mathematical description, this method of comparison should be effective and should not be sensitive to registration. A number of algorithms for extracting descriptors are discussed below.

Many types of equipment could be used to implement the invention and to perform the methods set forth above. One example of circuitry for performing these functions is described below.

III. Identification Systems

As noted above, the necessary equipment for performing iris recognition according to the invention could take many forms. The major functional components of any such system, however, will be those shown in FIG. 3, including illuminating means 70, imaging means 80 and comparing means 90.

Figures 8, 9:
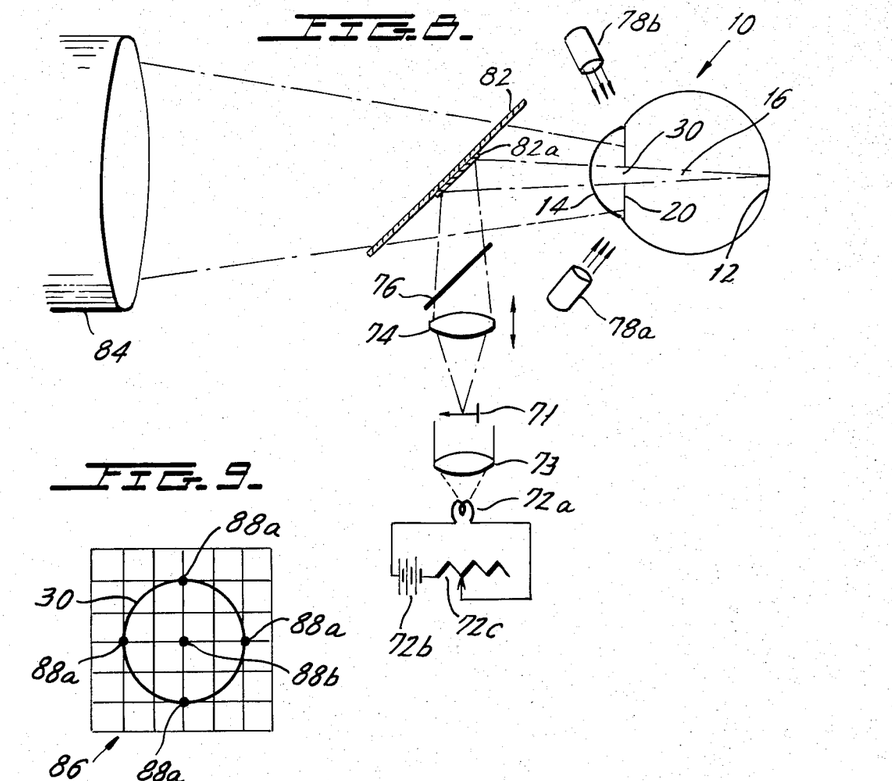
FIG. 8 is a schematic diagram showing the electrical and optical characteristics of a system according to the invention.
FIG. 9 is a plan view of a viewing screen for use in the system of FIG. 8.

FIG. 8 shows a system for illuminating and obtaining an image of the eye. The system includes a simplified electrical circuit for controlling illumination and an optical arrangement in which the image of fixation target 71 seen by eye 10 and the reflected image of iris 20 and pupil 30 to camera 84 are approximately coaxial. It is presently preferred to provide a target image, upon which eye 10 may be fixated, concentric with visual axis 16 for reference purposes. It is also preferred for camera 84 to capture the reflected image concentric or nearly concentric with visual axis 16, because if the image were obtained far from the axis 16, it would be distorted, which would then have to be compensated by appropriate processing. Additional illumination of iris 20 is provided obliquely to create good shadows of elevation-dependent features.

In the system of FIG. 8, the source of light is a filament 72a which receives power from power source 72b connected in series through variable resistor 72c, which may be an electrically controlled potentiometer. The light emitted by filament 72a is collimated by lens 73 and illuminates target 71, which may have any appropriate shape.

The image of target 71 is then focused by movable lens 74 and transmitted through monitor beam-splitter 76 onto axial beam-splitting plane 82. The image is then reflected from the central mirrored area 82a through pupil 30 onto retina 12.

The optical system shown in FIG. 8 includes means for placing target 71 at any desired optical distance from eye 10. Target 71 can thus be made visible to subjects with a wide variety of refractive states. The refraction or bending of light rays at the air interface of cornea 14, for example, is substantial and varies for different subjects. The necessary adjustment of optical distance is obtained by moving lens 74 toward or away from target 71 until target 71 is optically conjugate with retina 12. If necessary to compensate for astigmatism, lens 74 may also be a variable sphero-cylindrical lens system of any of the well-known types. Target 71 will be optically conjugate with retina 12 when, as shown in FIG. 8, the light from each point on target 71 comes to a focus at a corresponding point on retina 12. The convergence or divergence of light from target 71 due to the adjustment of lens 74 will thus compensate for the optics of eye 10.

Oblique light sources 78a and 78b provide illumination to the iris 20 and may be controlled similarly to filament 72a by using a variable resistor (not shown). The resulting reflection will depend on the positioning of oblique light sources 78a and 78b, because the iris is a diffuse reflector, reflecting light according to a cosine law in which the amount of reflected light in the direction normal to the iris varies as the cosine of the incident angle of the light.

Axial beam-splitting plane 82 serves the two functions of directing the image of target 71 from lens 74 toward eye 10 and also transmitting the reflected image of iris 20 to camera 84. In the arrangement shown in FIG. 8, which is not to scale, beam splitting plane 82 is a thin transparent sheet such as glass on which mirror 82a is formed for reflecting the image. Mirror 82a may be a microscopically thin, reflective film or coating, such as a metal, on the central part of plane 82 and on the side toward eye 10, to provide a first surface mirror. It may, for example, have an elliptical shape. The reflected image of target 71 is directed through pupil 30 onto the retina 12 of eye 10 to control the size of pupil 30. The reflected light from iris 20, which will emerge from eye 10 quite divergently, may pass through the clear, transparent area of beam splitting plane 82 which surrounds mirror 82a. Mirror 82a, however, will create a non-transparent area in the center of plane 82, preventing an intense reflection of the target image from cornea 14 from reaching camera 84. Since the reflected target image may be the brightest object in the field of view of camera 84, this may significantly reduce the noise in the image of iris 20 and pupil 30. Monitor beam-splitter 76 will provide an image of the intense reflection from cornea 14, as reflected by mirror 82a, and this reflection image may be used to position the eye according to known eye-positioning techniques. Proper positioning of the eye will help to provide a standardized image of iris 20 and pupil 30 and will ensure that the intense reflection of the target image does not reach camera 84.

FIG. 9 shows viewing screen 86 of camera 84, upon which are marked peripheral points 88a and central point 88b. Peripheral points 88a may be used to measure the size of pupil 30, as shown. When the perimeter of pupil 30 touches each of the peripheral points 88a, pupil 30 has been driven to a predetermined size at which an image should be obtained. Central point 88b may be useful in aligning pupil 30 so that size may be properly tested. As shown in FIG. 9, a grid may also be provided on viewing screen 86 to assist in the determination of the size of pupil 30 when it does not meet peripheral points 88a. Alternatively, concentric markings could be provided on screen 86, as disclosed in U.S. Pat. No. 3,966,310, issued to Larson.

It will be apparent from FIGS. 8 and 9 that the distance between camera 84 and eye 10 must be fixed in order to provide a standardized image. This can be done by providing a headrest (not shown) against which the forehead above eye 10 may be positioned. The headrest may also be equipped with appropriate additional surfaces for darkening a space around eye 10. This permits the system to provide a condition of nearly zero illumination to retina 12.

The system shown in FIGS. 8 and 9 may be manually operated to obtain the predetermined pupil size touching peripheral points 88a. First, variable resistor 72c is manually adjusted to its maixmum resistance, effectively turning off filament 72a. Oblique light sources 78a and 78b are activated to provide a desired level of illumination upon iris 20. Then, variable resistor 72c is gradually turned to a lower resistance until the image of target 71 begins to illuminate retina 12. The operator, looking at viewing screen 86, will see the pupil beginning to decrease in size as the illumination from filament 72a increases. When the perimeter of pupil 30, as seen through viewing screen 86, just touches peripheral points 88a, the operator may activate camera 84 to obtain an image of iris 20 and pupil 30. If further, predetermined sizes are marked by points in viewing screen 86, the operator may continue to adjust variable resistor 72c until those additional predetermined sizes of pupil 30 are shown in viewing screen 86 and are imaged when camera 84 is activated.

The optics of FIG. 8 cold be modified in many ways within the scope of the invention. For example, rather than providing a transparent beam-splitting plane 82 with a centered mirror 82a, the beam-splitting plane could be defined by two prisms positioned against each other or by a half-silvered mirror or other partially reflecting surface. Such arrangements, however, will result in a greater loss of intensity of the collimated light and of the reflected image than the arrangement of FIG. 8. If such an arrangement is desirable, therefore, it may be appropriate to provide additional illumination of the iris 20, as discussed below in relation to FIG. 11.

Figure 10:
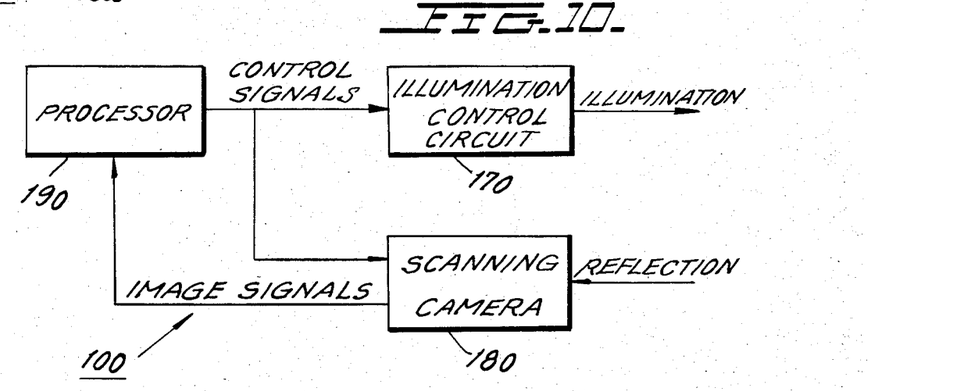
FIG. 10 is a functional block diagram of one embodiment of the system of FIG. 3.

FIG. 10 shows a block diagram of electrical components performing the functions set forth in FIG. 3. Iris recognition system 100 in FIG. 10 includes illumination control circuit 170, camera 180 and processor 190. Illumination control circuit 170 and camera 180 operate under the control of processor 190. In response to control signals, illumination control circuit 170 illuminates eye 10 both to control the size of pupil 30 and to provide a reflected image of iris 20 and pupil 30. This reflected image is received by camera 180, which may be a video camera which converts the reflected image into an image signal for processor 190. Processor 190 then compares the image signal with a reference image in order to identify the human being.

Figure 11:
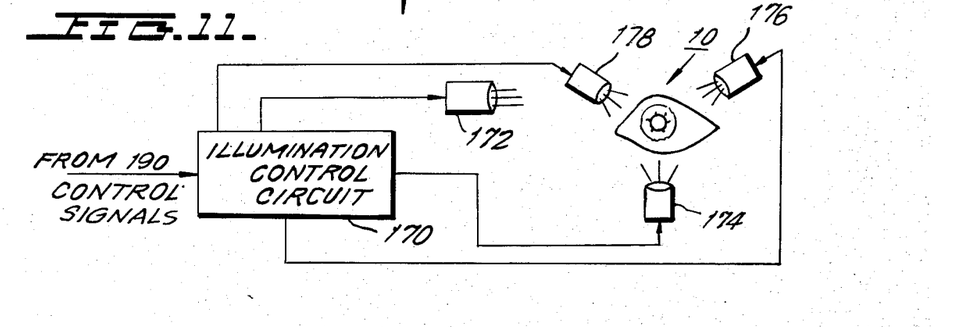
FIG. 11 is a diagram illustrating the illumination control circuit of FIG. 10.

FIG. 11 shows in greater detail the illumination system of iris recognition system 100. As shown in FIG. 11, illumination control circuit 170 controls light sources 172, 174, 176 and 178. In general, these light sources should be as small as possible to minimize noise in the reflected image from eye 10. Light source 172, which illuminates retina 12, as discussed in relation to FIG. 8, may do so through a fixation target 71 and a beam-splitting plane 82. Light source 172 will thus provide a target image upon which eye 10 will fix and focus, thereby becoming aligned for imaging. The target image should preferably be a distant object to discourage accommodation which would reduce pupil size. Rays from the target image may be relatively tightly collimated and subtend a small angle in order to provide a more critical, centralized alignment, or may be less tightly collimated if additional iris illumination is desired. The target image could also be compound, such as cross hairs in one plane which must be aligned on a designated part of a background at another plane to obtain alignment of the pupil, although this would depend on the acuity of the eye 10. Alternatively, a polarizing ring-sight device could be used to create concentric circles on the retina independent of the refraction of eye 10. The target image should not be extremely bright, because that would also reduce the size of pupil 30.

As mentioned above, the target image may be used to cause the subject to align pupil 30 for optimal imaging. In addition, however, it would be possible to provide an automatic alignment system using a feedback circuit and a servo-control mechanism to adjust the relative positions of the iris 20 and the camera 180. This adjustment of position could be accomplished with rotatable mirrors, plano-parallel plates, or prismatic devices such as Risley prisms. Alternatively, the head rest (not shown) can be moved in order to orient the head.

In addition to pupil-driving light source 172, the illumination system shown in FIG. 11 includes oblique light sources 174, 176 and 178. As discussed above in relation to FIG. 6, each of these oblique light sources 174, 176 and 178 may provide a relatively monochromatic beam of light, so that the shadows resulting from the oblique positioning of these light sources will lack the corresponding color, facilitating the subsequent processing of the shadow images. Each source 174, 176 and 178 could be a relatively monochromatic source such as an LED or a solid state laser.

Although FIG. 11 shows an arrangement in which three light sources are provided at approximately 120° angles from each other, the number of light sources and their relative angular positions could be varied in many ways. In addition, other arrangements could be used to obtain additional information about elevation-dependent features of iris 20. For example, more than one camera 180 could be provided, or a single camera 180 could be provided which could be moved between a plurality of positions in order to obtain three-dimensional information. Any other means for obtaining an image could be used, including laser-based techniques such as holography and including flying spot scanning by mechanical or electrooptical techniques.

Figure 12:
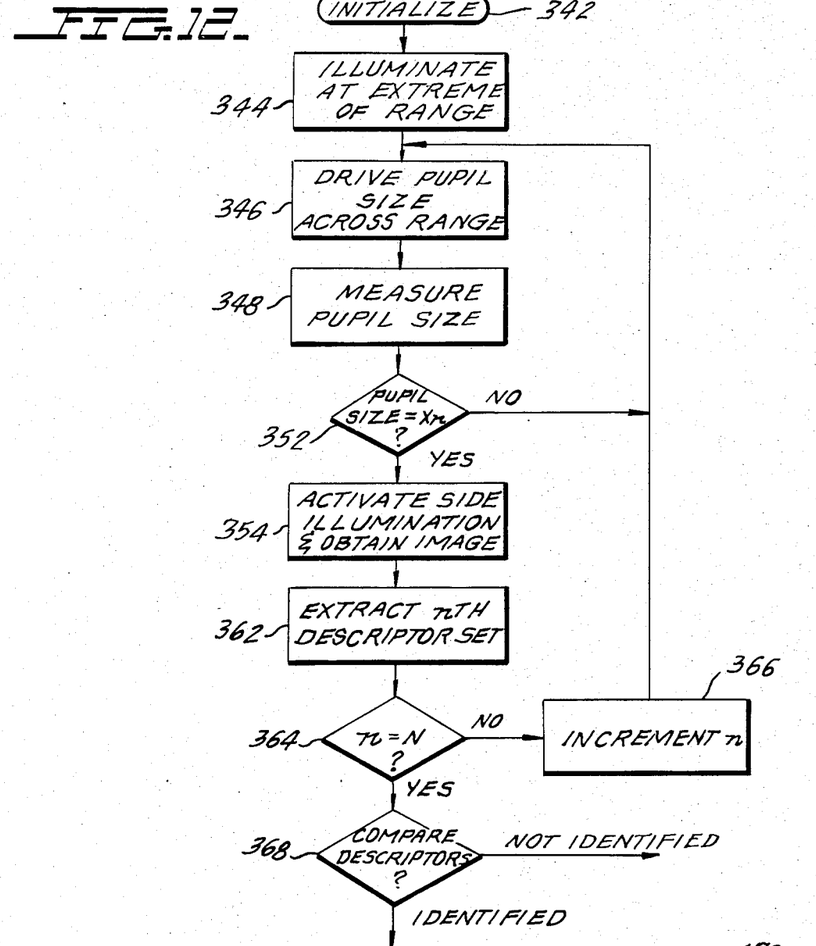
FIG. 12 is a flow chart of the operation of the processor of FIG. 10 according to the invention.

FIG. 12 shows a flow chart of the operation of processor 190 in FIG. 10. Processor 190 will at first be initialized in step 342, in order to provide appropriate memory contents and in order to perform the necessary loading of programs. In addition, as a part of initialization, processor 190 may provide control signals causing camera 180 to begin to operate and providing power to illumination control circuit 170. In step 344, processor 190 provides control signals to illumination control circuit 170 causing pupil-driving light source 172 to illuminate the retina 12 at the extreme illumination of the range available. In addition, oblique light sources 174, 176 and 178 may be activated to provide sufficient illumination so that camera 180 is able to provide an image of pupil 30 to processor 190.

When the extreme size of the pupil has been obtained in step 344, the pupil is then driven across the range of its size in step 346. This is performed by gradually increasing the illumination from pupil-driving light source 172. After each increase in intensity, the pupil size is measured in step 348 and tested in step 352 to determine whether it equals the desired predetermined size $x_n$. For the first iteration, the first predetermined size $x_1$ will be obtained after the necessary reiteration of the loop including steps 346, 348 and 352. Oblique light sources 374, 376 and 378 will also be activated, either at the same time or in sequence according to a method like that shown in FIG. 6, in order to obtain an image of the iris 20 and pupil 30 of eye 10. Oblique light sources 374, 376 and 378 should be activated in a way which minimizes the constriction of pupil 30. Therefore, it may be necessary to activate them before or while the illumination from light source 172 is increased.

From this image, processor 190 will then extract the nth descriptor set in step 362. For the image obtained when the pupil size is $x_1$, the first descriptor set will be obtained. Then, in step 364, n is tested to determine if it is equal to N, the total number of descriptor sets to be obtained. If not, n is incremented in step 366, and the loop including steps 346, 348, 352, 354, 362 and 364 is repeated for the next value of n. This loop will be repeated until step 364 determines that n equals N.

When n equals N, the resulting descriptor sets are compared with one or more reference descriptor sets in step 368. If the objective is to determine whether the eye 10 is that of one of a population of people, each descriptor set resulting from step 362 will be compared with the corresponding descriptor sets of the members of that population. On the other hand, if the objective is simply to confirm that an eye 10 is that of a specific individual, it is only necessary to compare the descriptor sets resulting from step 362 with the corresponding descriptor set of that individual, which may, for example, be stored on a credit card, identification card, or other identifying document, or in the memory of a computer system to which the processor 190 has access.

Upon the completion of step 368, an appropriate indication may be provided to the operator of iris recognition system 100 that the eye 10 has been identified or has not been identified, completing the operation shown in FIG. 12. At this point, the operator may choose to initiate further iris recognition by repeating the process shown in FIG. 12.

Processor 190, in extracting descriptors in step 362, may perform a wide variety of algorithms. A number of such algorithms are set forth in Ballard, D. H. and Brown, C. M., *Computer Vision*, Prentice-Hall, Englewood Cliffs, N.J., 1982; Duda; R. O. and Hart, P. E., *Pattern Recognition and Scene Analysis*, Wiley, New York, 1973; and Rosenfeld, A., *Digital Picture Processing*, Academic Press, New York, 1982. Many of these algorithms use classical mathematical techniques such as difference operators, taking a differential equation of selected points and testing a rate of change, and mask matching or surface fitting, fitting to a known shape at various orientations. Although these and other such algorithms are known, they have not previously been applied to the specific features of the iris and pupil.

The location, size and deviation from circularity of the pupil could provide a number of descriptors. The pupil could first be detected using a boundary detection algorithm or an edge detection algorithm, which may, for example, detect an abrupt gray level change. Systems performing pupil size measuring algorithms are disclosed, for example, in U.S. Pat. No. 3,598,107, issued to Ishikawa et al, and U.S. Pat. No. 3,533,683, issued to Stark et al. A Hough transform algorithm for detecting circles, which maps curves into the transform space according to characteristics such as curvature, could be used on a boundary or edge which is detected. Alternatively, the received image could be subjected to a thresholding algorithm after which a region-growing or aggregation algorithm, such as the blob coloring algorithm discussed by Ballard and Brown, could be performed to find the largest connected region of pixels with intensity values below threshold. Since the pupil is central, the region could be grown outward from a central dark pixel in the image, progressively aggregating the adjacent dark pixels until the pupil boundary is reached, beyond which adjacent pixels will not be dark. This will provide a measure both of pupil size and of location, as the center of the pupil may be determined from its boundary. This may be done, for example, by taking slices through the dark region in a number of radial directions to select a largest diameter. To eliminate the chance that the largest diameter is not the true diameter, as, for example, if it extended to a notch or other irregularity in the boundary, the least sum of squares from its center to the boundary could be taken and compared with that of the second largest diameter. The center and radius giving the least sum of squares would define the circle most closely approximating the pupil boundary, and the residual sum of squares would be a quantitative measure of deviation of the pupil from circularity, a "figure of merit" for the pupil. This figure of merit would be a useful descriptor of the pupil.

The characteristics of the radial furrows could also be used to obtain descriptors. From the center of the pupil, the precision of radiality of the radial furrows can be obtained. Line detection algorithms and streak or thick line detection algorithms could be used to locate the radial furrows. The radial furrows may then be compared with true straight lines radiating from the center by obtaining a sum of squares of differences, indicating radiality. Some furrows, rather than being entirely straight, include, for example, two offset parts, each of which is generally radial, the two being connected by a non-radial jog. A measure of thickness could be obtained for such a furrow by determining how wide a streak is necessary to cover the furrow. Also, the Hough transform algorithm for detecting straight lines could be applied to obtain such descriptors as the length, angular location and direction of radial furrows.

The concentric furrows may be detected and described using edge detection algorithms and the Hough transform algorithms for detecting curved lines. Similarly, the collarette and the contours of the crypts along it could be described using edge detection algorithms and chain coding algorithms. In addition, points of high curvature along these contours could be located and represented for matching purposes, which may be more efficient. Isolated crypts could be described by a thresholding algorithm, followed by a region-growing algorithm and then algorithms obtaining the center of gravity and the lower order central moments, as described by Duda and Hart.

Spot detection algorithms, detecting high contrast spikes in areas of relatively constant gray level, could detect small pigment spots. More generally, algorithms like those for measuring the pupil could be used to obtain location and lower-order central moments of pigment spots, and other such features. Also, high-curvature points along the contour of a feature could be detected and described.

Finally, the color of the iris generally could be found by an algorithm obtaining a histogram in a three-dimensional RGB (Red-Green-Blue) color space, as described by Ballard and Brown at page 153. The peak in the histogram will provide a descriptor of color.

As noted above, the embodiment of FIGS. 8–12 could be modified in many ways within the scope of the invention. Processor 190 may control the operation of illumination control circuit 170 and camera 180 in any appropriate manner to obtain images for processing. For example, the image from camera 180 may be constantly received and processed by processor 190 to determine the appropriate level of illumination by illumination control circuit 170. At the same time, when it is desired to obtain an image at one of the predetermined sizes of pupil 30, processor 190 may control illumination means 170 to maintain a temporarily constant level of illumination while camera 180 obtains a complete image for processing.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. A method of identification of a person, comprising:

storing image information of at least a portion of the iris and pupil of the person's eye;

illuminating an eye, of an unidentified person having an iris and a pupil;

obtaining at least one image of at least the same portion of the iris and pupil of the eye of the unidentified person; and comparing at least the iris portion of the obtained image with the stored image information to identify the unidentified person.

2. The method of claim 1 in which illuminating comprises driving the pupil of the eye to at least one predetermined size, comparing at least the iris portion of the obtained image with stored image information obtained from an eye with its pupil having the same predetermined size.

3. The method of claim 2 in which driving the pupil comprises directing light onto the retina of the eye and adjusting the intensity of the light until the pupil reaches the predetermined size.

4. The method of claim 2 in which driving the pupil comprises driving the pupil to a plurality of the predetermined sizes; the step of obtaining at least one image comprising obtaining a respective image at each of the predetermined sizes of the pupil.

5. The method of claim 4 in which illuminating comprises changing the intensity of illumination at a predetermined rate between at least two of the predetermined pupil sizes and measuring a rate of change of pupil size as the illumination intensity changes.

6. The method of claim 1 in which illuminating comprises illuminating the iris obliquely for providing shadows of elevation-dependent features.

7. The method of claim 6 in which illuminating the iris obliquely comprises illuminating the iris from a plurality of spatially separated light sources for providing shadows of elevation dependent features extending in a plurality of directions.

8. The method of claim 7 in which illuminating the iris from a plurality of spatially separated light sources comprises illuminating the iris from a plurality of relatively monochromatic light sources, each light source providing shadows lacking a corresponding color of light.

9. The method of claim 1 in which comparing the obtained image with the stored image information comprises comparing at least the iris portion of the obtained image with a stored reference image for identifying the person.

10. The method of claim 1 in which comparing the obtained image with stored image information comprises deriving a set of descriptors of at least the iris portion of the obtained image and comparing the derived descriptors with stored reference descriptors derived from a previous image for identifying the person.

11. The method of claim 10 in which deriving a set of descriptors comprises deriving descriptors of the pupil.

12. The method of claim 10 in which deriving a set of descriptors comprises deriving descriptors of a pigment frill around the pupil.

13. The method of claim 10 in which deriving a set of descriptors comprises deriving descriptors of a collarette in the iris.

14. The method of claim 10 in which deriving a set of descriptors comprises deriving descriptors of at least one concentric furrow in the iris.

15. The method of claim 10 in which deriving a set of descriptors comprises deriving descriptors of at least one radial furrow in the iris.

16. The method of claim 10 in which deriving a set of descriptors comprises deriving descriptors of at least one crypt in the iris.

17. The method of claim 10 in which deriving a set of descriptors comprises deriving descriptors of at least one pigment spot in the iris.

18. The method of claim 10 in which deriving a set of descriptors comprises deriving descriptors of at least one atrophic area in the iris.

19. The method of claim 10 in which deriving a set of descriptors comprises deriving descriptors of at least one tumor in the iris.

20. The method of claim 10 in which deriving a set of descriptors comprises deriving descriptors of at least one congenital filament in the iris.

21. A system of identification, comprising:
means for storing an image of at least a portion of the iris and pupil of a person's eye;
means for illuminating an eye having an iris and a pupil;
means for obtaining an image of at least the same portion of the iris and pupil of the eye; and
means for comparing at least the iris portion of the obtained image with the stored image information to identify the person.

22. The system of claim 21 in which the means for illuminating comprises an adjustable light source for illuminating the eye at a selected value in a range of light intensity.

23. The system of claim 22 in which the means for illuminating further comprises control means responsive to at least the iris portion of the obtained image of the eye for detecting the size of the pupil and operable for adjusting the adjustable light source to a selected light intensity for controlling the size of the pupil.

24. The system of claim 23 in which the control means is further operable for controlling the size of the pupil to obtain a plurality of predetermined pupil sizes; the control means being further operable for adjusting the light source at a predetermined rate across the range of light intensity between at least two of the predetermined pupil sizes for measuring the rate of change of pupil sizes as the light intensity is adjusted.

25. The system of claim 21 in which the illuminating means further comprises a plurality of spatially separated oblique light sources for illuminating the iris obliquely.

26. The system of claim 25 in which each of the oblique light sources comprises a relatively monochromatic light source for providing shadows lacking a corresponding color of light.

27. The system of claim 26 in which each relatively monochromatic light source comprises a laser.

28. The system of claim 21 in which the image obtaining means comprises a camera, the comparing means comprising a processor responsive to an output from the camera for comparing the obtained image with stored image information.

29. The system of claim 28 in which the processor comprises storage means for storing reference descriptors derived from a previous image, the processor being operable for deriving a set of descriptors of the obtained image and for comparing the derived descriptors with the reference descriptors for identifying the person.

30. The system of claim 21 in which the image obtaining means comprises a laser.

31. The system of claim 21 further including target means for providing an object upon which the eye fixates.

32. The system of claim 31 further including focusing means for focusing the target means.

* * * * *